United States Patent
Oki et al.

(10) Patent No.: US 9,931,519 B2
(45) Date of Patent: Apr. 3, 2018

(54) MEDICAL APPARATUS, THERAPY APPARATUS, METHOD OF ESTIMATING OPTICAL PROBE, AND CALIBRATION METHOD

(71) Applicant: Sony Corporation, Tokyo (JP)

(72) Inventors: Tomoyuki Oki, Kanagawa (JP); Shiho Hakomori, Kanagawa (JP)

(73) Assignee: SONY CORPORATION, Tokyo (JP)

( * ) Notice: Subject to any disclaimer, the term of this patent is extended or adjusted under 35 U.S.C. 154(b) by 188 days.

(21) Appl. No.: 13/653,163

(22) Filed: Oct. 16, 2012

(65) Prior Publication Data
US 2013/0102861 A1    Apr. 25, 2013

(30) Foreign Application Priority Data

Oct. 19, 2011 (JP) ................. 2011-229444

(51) Int. Cl.
*A61B 17/58* (2006.01)
*G01J 1/00* (2006.01)
*A61B 5/00* (2006.01)
*A61N 5/06* (2006.01)
*A61N 5/067* (2006.01)

(52) U.S. Cl.
CPC ............ *A61N 5/062* (2013.01); *A61N 5/0601* (2013.01); *A61N 5/0616* (2013.01); *A61N 2005/063* (2013.01); *A61N 2005/067* (2013.01); *A61N 2005/0628* (2013.01); *A61N 2005/0644* (2013.01); *A61N 2005/0652* (2013.01)

(58) Field of Classification Search
CPC ............ A61N 5/062; A61N 2005/0652; A61N 5/0601; A61N 2005/067; A61N 5/0616; A61N 2005/0644

USPC .................... 607/88, 89; 356/213; 600/314
See application file for complete search history.

(56) References Cited

U.S. PATENT DOCUMENTS

| 5,192,278 | A   | *   | 3/1993 | Hayes   ................ A61B 18/245 606/15 |
| 6,214,033 | B1  | *   | 4/2001 | Ii   ........................... A61N 5/062 604/20 |
| 6,792,018 | B2  | *   | 9/2004 | Couch   ....................... 372/38.02 |
| 6,930,314 | B2  | *   | 8/2005 | Jackson, III   ....... G01N 21/6456 250/458.1 |
| 7,920,908 | B2  | *   | 4/2011 | Hattery et al.   ............... 600/407 |
| 2001/0003800 | A1 | * | 6/2001 | Crowley   ....................... 607/88 |
| 2005/0113890 | A1 | * | 5/2005 | Ritchie et al.   ................. 607/88 |
| 2005/0152146 | A1 | * | 7/2005 | Owen et al.   .................. 362/294 |
| 2006/0020260 | A1 | * | 1/2006 | Dover et al.   ..................... 606/9 |

FOREIGN PATENT DOCUMENTS

| JP | 2003-010232 | 1/2003 |
| JP | 2004-350933 | 12/2004 |

* cited by examiner

*Primary Examiner* — William Thomson
*Assistant Examiner* — Sebastian X Lukjan
(74) *Attorney, Agent, or Firm* — K&L Gates LLP

(57) ABSTRACT

According to an embodiment of the present application, there is provided a medical apparatus, including: a light source unit configured to be capable of emitting light including at least natural emission light, the light being guided into an optical probe; a first detecting unit configured to detect an intensity of light exiting from the light source unit; and a calculation unit configured to calculate to approximate to a non-linear function based on an intensity of light detected by the first detecting unit for calibration of the optical probe.

10 Claims, 14 Drawing Sheets

MEDICAL APPARATUS, THERAPY APPARATUS, METHOD OF ESTIMATING OPTICAL PROBE, AND CALIBRATION METHOD

CROSS REFERENCES TO RELATED APPLICATIONS

The present application claims priority to Japanese Priority Patent Application JP 2011-229444 filed in the Japan Patent Office on Oct. 19, 2011, the entire content of which is hereby incorporated by reference.

BACKGROUND

The present disclosure relates to a medical apparatus, a therapy apparatus, a method of estimating an optical probe, and a calibration method used, for example, for a therapy, in which a photodynamic therapy is employed, and to monitor pharmaceutical concentration.

Basic examinations of medical laser apparatuses were started in the 1960s. Subsequently, laser-therapy apparatuses using a $CO_2$ laser, an ND:YAG laser, an Ar ion laser, a ruby laser, and the like were developed and were widely used in the 1970s. An apparatus having a semiconductor laser as a light source is being developed as a next-generation apparatus. A semiconductor laser is capable of being downsized, is easily maintained, and is easily managed. As the laser technology is developed and as the pharmaceutical studies are developed, Photo Dynamic Therapy (PDT) is attracting attention in recent years. In Photo Dynamic Therapy (PDT), a fluorescence pharmaceutical, which is laser-light-sensitive, is accumulated in a certain cell. After that, the cell is irradiated with the laser light, and the inside of the cell is broken. PDT is developed mainly in the field of pulmonary cancer and brain tumor. Laser apparatuses such as an excimer dye laser (Hamamatsu Photonics K.K.) and a laser apparatus for PDT (Panasonic Corporation) are widely used.

If a laser-therapy apparatus accurately determines the amount of emitted light output during a therapy, the following risks may be avoided. That is, a risk of giving needless irradiation energy to a diseased site, and a risk of not obtaining a therapeutic effect because of lack of irradiation energy, may be avoided. In PDT, a risk of administering excessive fluorescence pharmaceutical may also be avoided. To accurately determine the amount of emitted light output during a therapy is one of the important technologies to provide a safer and more accurate therapy.

Meanwhile, in a PDT laser-therapy apparatus, a light-emitting portion (optical probe) contacts a living body. Because of this, an optical probe is exchanged for each procedure, normally. In most cases, an optical probe has an internal optical fiber, and the optical fiber transmits light. The conductivity greatly depends on individual differences of probes.

In view of this, Japanese Patent Application Laid-open No. 2004-350933 describes a technology in which individual information is input in an optical probe, and in which a light power is calibrated based on the individual information when the optical probe is connected. Japanese Patent Application Laid-open No. 2003-10232 discloses a technology in which a light power is calibrated by using a product individual identification. However, in those technologies, information on an optical probe is not one immediately before use and may not include change in property because of sterilization, transport, and installation processes.

SUMMARY

In PDT, it is necessary to emit light with a low power (several mW or less), which exhibits no therapeutic effect, and to sense pharmaceutical concentration in blood in real time.

The inventors calibrated a light power immediately before use by emitting light with the range of the low power, which exhibits no therapeutic effect. However, the calibration was not accurately performed.

In view of the above-mentioned circumstances, it is desired to provide a medical apparatus, a therapy apparatus, a method of estimating an optical probe, and a calibration method, which are capable of performing accurate calibration even in the case of emitting light with a low power.

According to an embodiment of the present application, there is provided a medical apparatus, including: a light source unit configured to be capable of emitting light including at least natural emission light, the light being guided into an optical probe; a first detecting unit configured to detect an intensity of light exiting from the light source unit; and a calculation unit configured to calculate to approximate to a non-linear function based on an intensity of light detected by the first detecting unit for calibration of the optical probe.

According to the present application, the calculation unit calculates to approximate to a non-linear function based on an intensity of light guided into the optical probe. Based on the calculate result, the optical probe is calibrated. Therefore, calibration is accurately performed even in a case of emitting light with a low power.

According to the present application, the light source unit may include a semiconductor laser, and the calculation unit may be configured to, in a case where the semiconductor laser emits light including laser light, calculate to approximate to a non-linear function based on an intensity of light detected by the first detecting unit for calibration of the optical probe.

According to the present application, the semiconductor laser not only emits laser light but also emits natural emission light during low-power emission. Calibration is accurately performed in a wide-power bandwidth from natural emission light to laser light.

According to the present application, the calculation unit may be configured to determine whether the semiconductor laser emits light including the natural emission light or the semiconductor laser emits light including the laser light, based on a laser-oscillation-threshold current from the semiconductor laser.

According to the present application, it is possible to accurately determine whether the semiconductor laser emits laser light or natural light. Calibration is accurately performed in a wide-power bandwidth.

According to the present application, the medical apparatus may further include: a guide unit, to which the optical probe is attachable, configured to guide light emitted from the light source unit to the attached optical probe; and a second detecting unit configured to detect an output of light exiting from the optical probe attached to the guide unit, The calculation unit may be configured to obtain a correlation between an intensity of light detected by the first detecting unit and an output of light detected by the second detecting unit, based on calculation to approximate to the non-linear function.

According to the present application, the calculation unit may be configured to calculate an output of light exiting from the optical probe based on an intensity of light detected by the first detecting unit by using the obtained correlation.

According to the present application, the medical apparatus may further include: a display unit configured to display an output of light exiting from the optical probe, the output of light being calculated by the calculation unit; and an operation unit configured to be capable of receiving an operation to adjust an output of light emitted from the light source unit. As a result, it is possible to accurately perform a procedure in real time.

According to another embodiment of the present application, there is provided a therapy apparatus, including: a semiconductor laser; a guide unit, to which one end of an optical probe is attachable, configured to guide light from the semiconductor laser to the one end; a calibration unit, to which the other end of the optical probe is inserted when calibrating the optical probe, configured to detect an output of light from the other end; and a calculation unit configured to obtain a correlation between an intensity of light from the semiconductor laser and an output of light detected by the calibration unit, based on calculation to approximate to a non-linear function when the semiconductor laser emits laser light, and based on calculation to approximate to a linear function when the semiconductor laser emits natural emission light.

According to another embodiment of the present application, there is provided a method of estimating an optical probe, including: introducing light into one end of an optical probe; guiding light out of the other end of the optical probe; and obtaining a correlation between an intensity of the introduced light and an output of the guided light for each optical probe, based on calculation to approximate to a non-linear function.

Here, the method of estimating an optical probe may further include obtaining a correlation between an intensity of the introduced light and an output of the guided light based on calculation to approximate to a linear function, in a case where light introduced into the optical probe is laser light.

According to another embodiment of the present application, there is provided a calibration method, including: guiding light from a semiconductor laser into one end of an optical probe; detecting an output of light from the other end of the optical probe; and obtaining a correlation between an intensity of light from the semiconductor laser and the detected output of light, based on calculation to approximate to a non-linear function when the semiconductor laser emits laser light, and based on calculation to approximate to a linear function when the semiconductor laser emits natural emission light.

As described above, according to the present application, calibration is accurately performed even in a case of emitting light with a low power.

These and other objects, features and advantages of the present disclosure will become more apparent in light of the following detailed description of best mode embodiments thereof, as illustrated in the accompanying drawings.

Additional features and advantages are described herein, and will be apparent from the following Detailed Description and the figures.

BRIEF DESCRIPTION OF THE FIGURES

FIG. 11 is sterilized and packed;

DETAILED DESCRIPTION

Hereinafter, embodiments of the present disclosure will be described with reference to the drawings.

Configuration of PDT Laser-Therapy Apparatus

Figure 1:
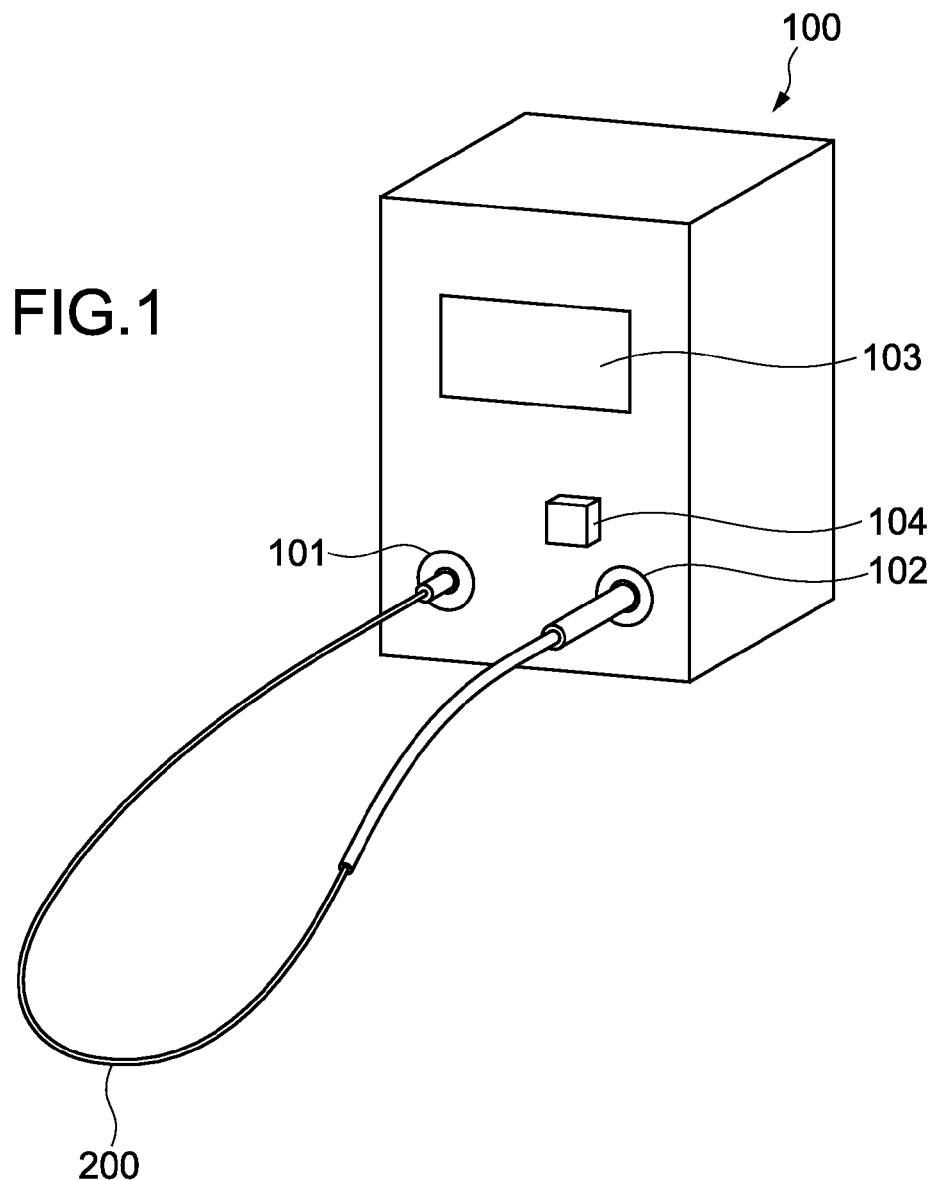
FIG. 1 is a perspective view showing an outer appearance of a PDT laser-therapy apparatus for atrial fibrillation according to an embodiment of the present application.
Figure 2:
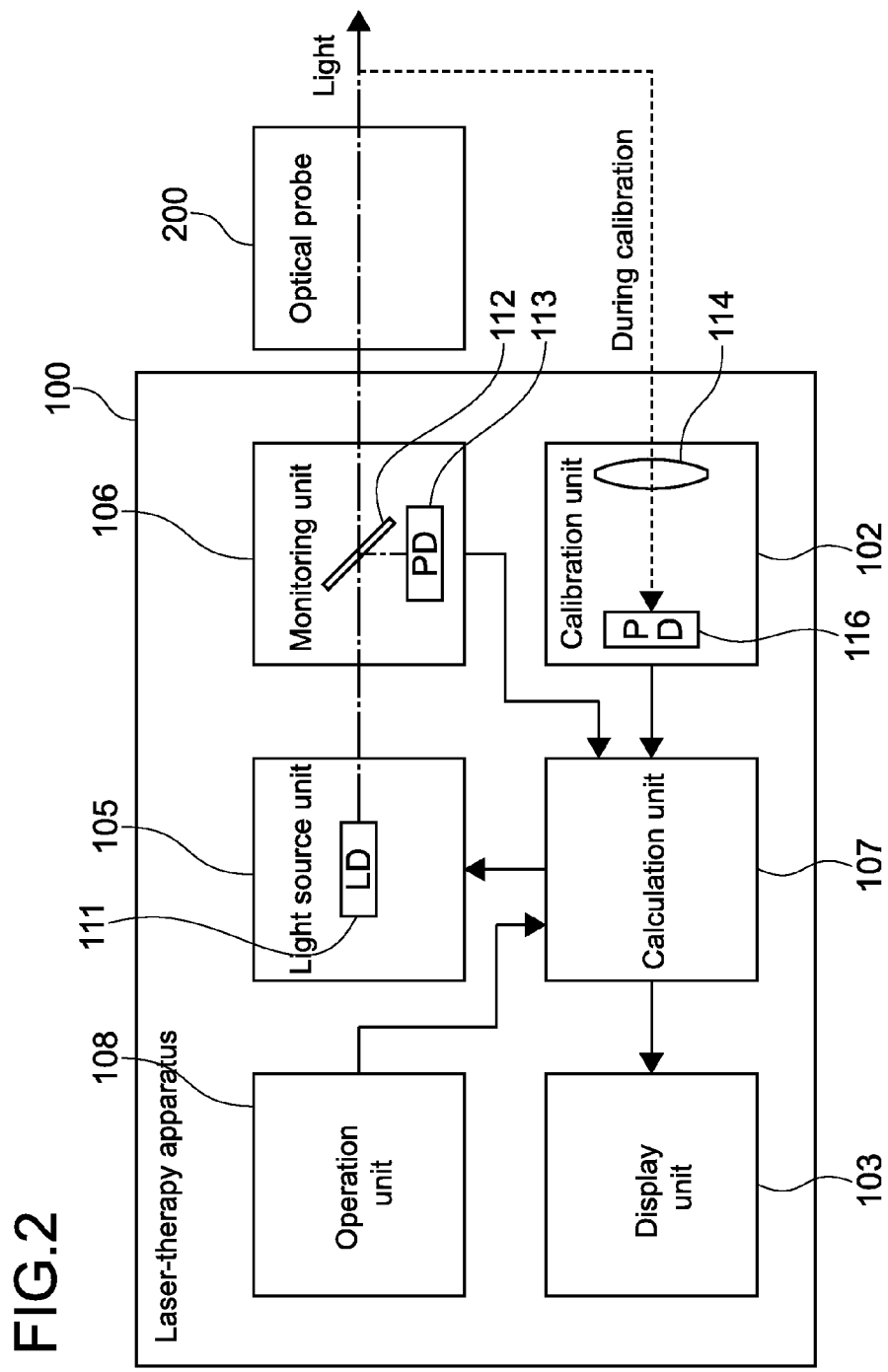
FIG. 2 is a block diagram showing the configuration of a PDT laser-therapy apparatus of FIG. 1.

FIG. 1 is a perspective view showing an outer appearance of a PDT laser-therapy apparatus for atrial fibrillation according to an embodiment of the present application. FIG. 1 shows a state where an optical probe is being calibrated by using the PDT laser-therapy apparatus. FIG. 2 is a block diagram showing the configuration of a PDT laser-therapy apparatus 100.

As shown in FIG. 1 and FIG. 2, the PDT laser-therapy apparatus 100 as a medical apparatus includes a guide unit 101, a calibration unit 102 as a second detecting unit, a display unit 103, and an unlock button 104. The PDT laser-therapy apparatus 100 further includes a light source unit 105, a monitoring unit 106 as a first detecting unit, a calculation unit 107, and an operation unit 108. The PDT laser-therapy apparatus 100 outputs not only light including laser light, but also light including low-power natural emission light. The light including laser light is mainly used for therapy. The light including natural emission light is mainly used to monitor pharmaceutical concentration.

The light source unit 105 includes a, for example, AlGaInP-series high-power semiconductor laser 111. A semiconductor laser is not limited to this. Alternatively, for example, GaN-series semiconductor laser or the like may be used. Light exiting from the light source unit 105 is transmitted to an optical probe 200 via the monitoring unit 106 and the guide unit 101.

A light guiding unit 201 of the optical probe 200 is attached to/detached from the guide unit 101. The light guiding unit 201 guides light, which exits from the light source unit 105, into the attached optical probe 200.

The monitoring unit 106 detects intensity of light, which is guided into the optical probe 200 attached to the guide unit 101. That is, the monitoring unit 106 detects intensity of light, which is output from the light source unit 105 and is guided into the guide unit 101. The monitoring unit 106 includes, for example, a half mirror 112, and a monitoring photodiode (PD) 113. The half mirror 112 is disposed in the optical path of light, which is output from the light source unit 105 and is guided into the guide unit 101, and extracts part of the light. The extracted light is guided into the monitoring photodiode 113. The monitoring photodiode 113 detects intensity of light guided from the guide unit 101 into the optical probe 200, based on the part of the light extracted by the half mirror 112. In this embodiment, the half mirror 112 is used to extract light. Alternatively, another optical device such as a beam splitter or a sampler may be used, as a matter of course.

A monitored value of output light during operation is obtained based on an intensity of light detected by the monitoring photodiode 113. That is, the intensity of light detected by the monitoring photodiode 113 is assumed as output of light exiting from the tip of the optical probe 200 during operation. The intensity of light detected by the monitoring photodiode 113 is assumed as a monitored value during operation. However, correlation between the intensity of light detected by the monitoring photodiode 113 and the output of light exiting from the tip of the optical probe 200 is not always constant because of individual difference of the optical probe 200. In view of this, the PDT laser-therapy apparatus 100 performs calibration every time the optical probe 200 is attached.

In most cases, the optical probe 200 has an internal optical fiber, and the optical fiber transmits light. The conductivity greatly depends on individual differences of probes. That is, an output of light, which passes the optical probe 200 and exits from the tip, greatly depends on individual differences of the optical probe 200. Such an individual difference may lead to a risk of giving needless irradiation energy to a diseased site, a risk of not obtaining a therapeutic effect because of lack of irradiation energy, and a risk of administering excessive fluorescence pharmaceutical. The tip of an applicator 202 is inserted in the calibration unit 102 immediately before use of the optical probe 200, in order to calibrate an individual difference of the optical probe 200. A lock mechanism (not shown), which is provided on the calibration unit 102, is engaged with a groove of the like of a tip portion. In this state, the calibration unit 102 measures an output of light from the optical probe 200. Note that, by pressing the unlock button 104, the tip portion of the applicator 202 is detached from the calibration unit 102.

In order to measure an output of the light exiting from the optical probe 200, the calibration unit 102 collects light by means of a collecting device 114 such as an integrating sphere or a lens, receives light by means of the photodiode 116, and obtains the present value. Because the optical probe 200 is exchanged every procedure, the calibration process is performed every time the optical probe 200 is exchanged.

The calculation unit 107 calculates an intensity of light, which is detected by the monitoring unit 106, by using functions (described later) to calibrate the optical probe.

The display unit 103 displays, in real time, an output of light exiting from the calibrated optical probe 200. An operator operates the operation unit 108 and performs procedure while watching a value displayed on the display unit 103.

Based on the operation of the operation unit 108, current supplied to the semiconductor laser 111 is adjusted, and the output of light exiting from the semiconductor laser 111 is changed to a desired value.

As shown in FIG. 1, the above-mentioned calibration is performed as follows. The optical probe 200 attached to the guide unit 101 is inserted in the calibration unit 102. Light exits from the light source unit 105. The correlation between an intensity of light detected by the monitoring unit 106 and an output of light detected by the calibration unit 102 is obtained.

More specifically, current supplied to the semiconductor laser 111 is gradually increased, for example. A relation between an intensity of light detected by the monitoring unit 106 and an output of light detected by the calibration unit 102 is obtained at each of a plurality of points. A correlation is obtained from the result. In an actual therapy or the like, the monitoring unit 106 monitors an intensity of light, and an output of light exiting from the optical probe 200 is estimated based on the obtained correlation.

In the general semiconductor laser 111, a linear relation is established between a current supplied to the semiconductor laser 111 and an intensity of a laser light detected by the monitoring unit 106. Because of this, it has been thought that a relation between an intensity of light monitored by the monitoring unit 106 and an output of light exiting from the optical probe 200 is a linear relation.

Meanwhile, with the PDT laser-therapy apparatus 100, it is necessary to emit light with a low power (several mW or less), which exhibits no therapeutic effect, and to sense pharmaceutical concentration in blood in real time. The inventors have found out that calibration accuracy is extremely low in a case where calibration is performed assuming that a linear relation is established between an intensity of light monitored by the monitoring unit 106 and an output of light exiting from the optical probe 200.

Figure 3:
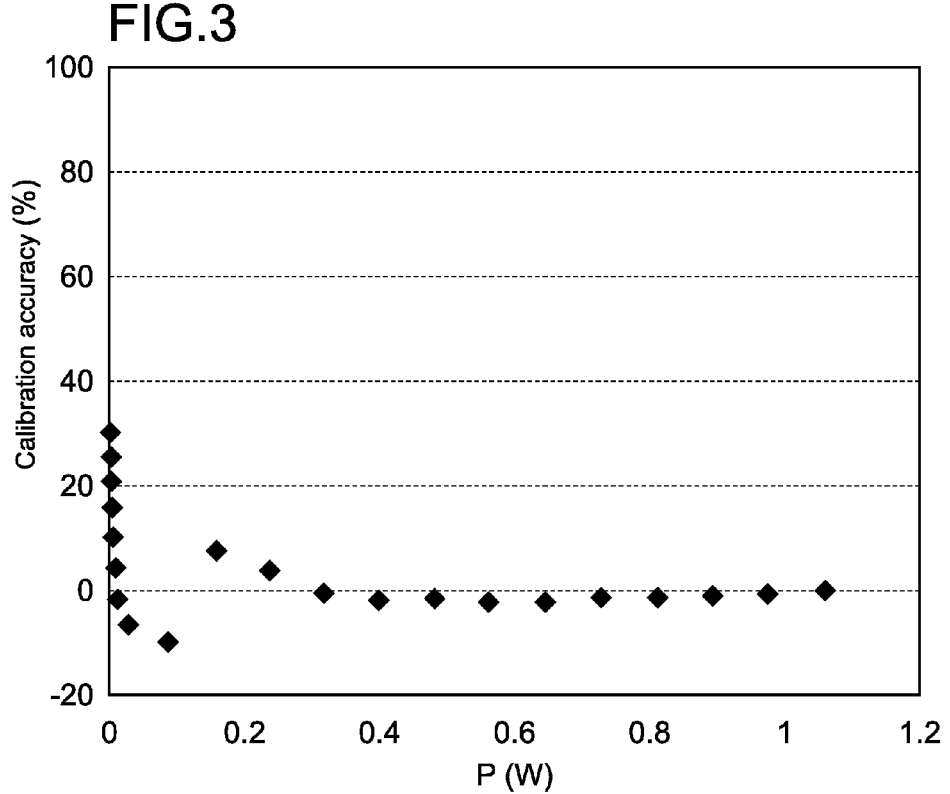
FIG. 3 is a graph showing calibration accuracy in a case where calibration is performed assuming that a linear relation is always established between an intensity of light monitored by a monitoring unit and an output of light exiting from an optical probe.

FIG. 3 shows calibration accuracy in a case where calibration is performed assuming that a linear relation is always established between an intensity of light monitored by the monitoring unit 106 and an output of light exiting from the optical probe 200. As shown in the result, calibration accuracy is extremely low in the low-power range (about 0.1 W or less). If calibration accuracy is such low, pharmaceutical concentration in, for example, blood may not be estimated accurately.

Figure 4:
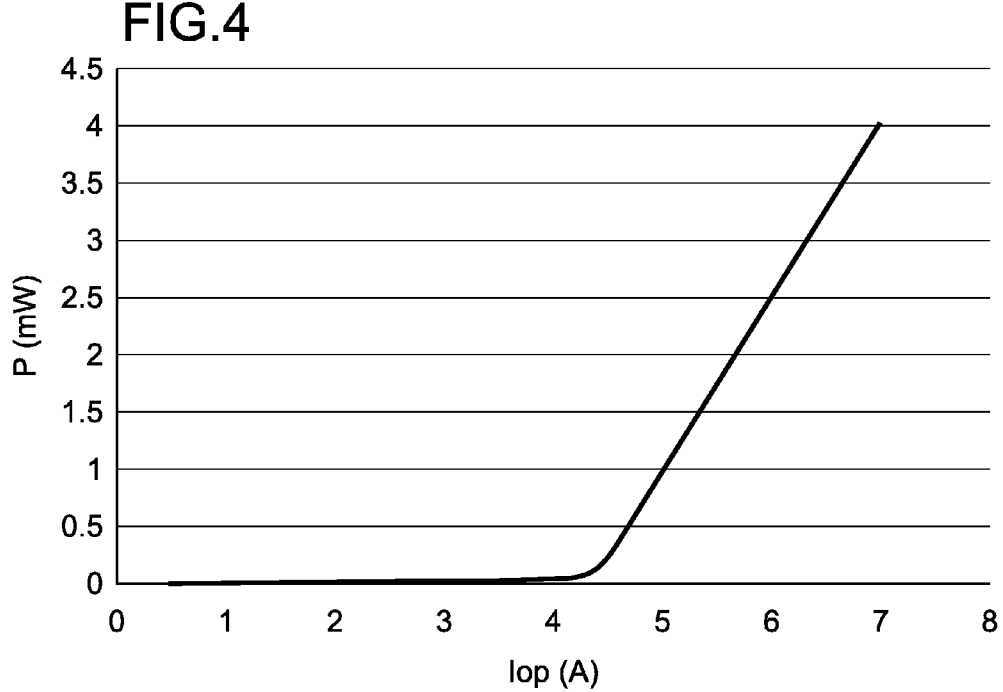
FIG. 4 is a graph showing a relation between a current supplied to a semiconductor laser and an output from a calibration unit.
Figure 5:
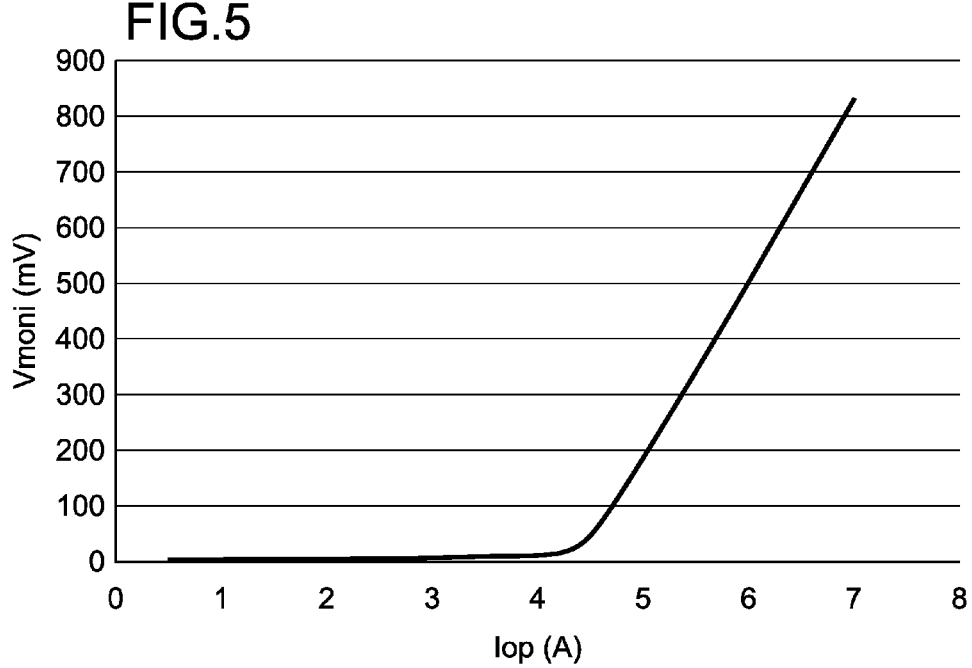
FIG. 5 is a graph showing a relation between a current supplied to the semiconductor laser and an output from a monitoring unit.
Figure 6:
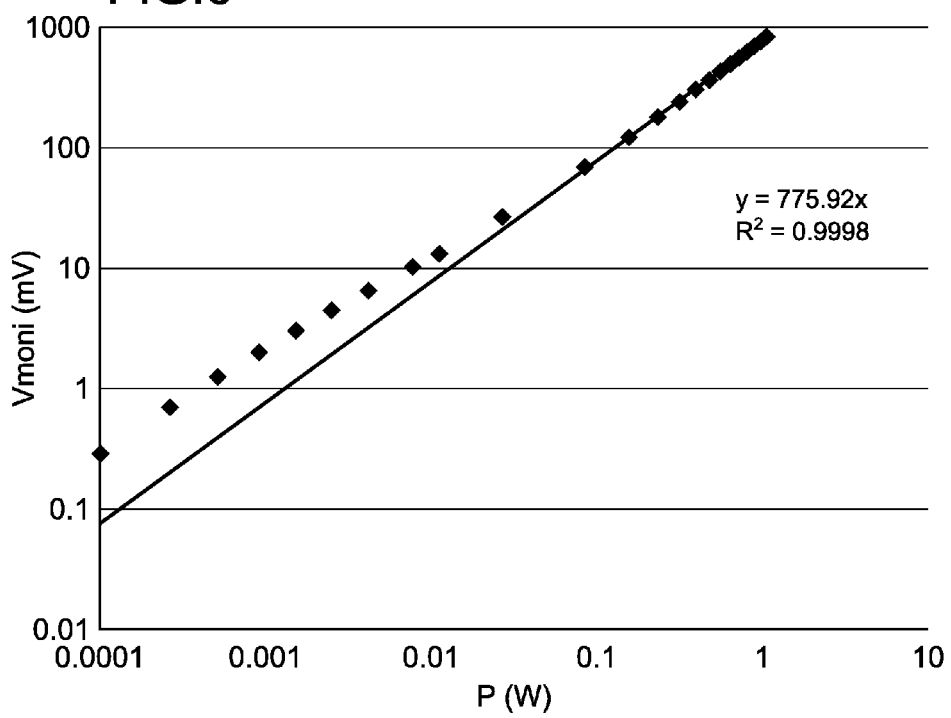
FIG. 6 is a graph showing a correlation between an output from the calibration unit and an output from the monitoring unit.

FIG. 4 shows a relation between a current Iop supplied to the semiconductor laser 111 and an output (present value: P) from the calibration unit 102. FIG. 5 shows a relation between a current Top supplied to the semiconductor laser 111 and an output (monitored value: Vmoni) from the monitoring unit 106. FIG. 6 shows a correlation between an output (present value: P) from the calibration unit 102 and an output (monitored value: Vmoni) from the monitoring unit 106 in this state.

As shown in FIG. 6, a relation between an output (present value: P) from the calibration unit 102 and an output (monitored value: Vmoni) from the monitoring unit 106 is not linear in a low-power range.

The inventors have found out that a reason therefor is that the semiconductor laser 111 does not laser-oscillate in a low-power range but outputs natural emission light. More specifically, the inventors have thought that there are the following reasons.

(1) The radiation angle of natural emission light is different from the radiation angle of laser light. Because of this, coupling efficiency of natural emission light with an optical fiber in the optical probe 200 is different from coupling efficiency of laser light with the optical fiber in the optical probe 200.

(2) The oscillation wavelength of natural emission light is larger than the oscillation wavelength of laser light. Because of this, natural emission light is affected by the wavelength property of the light source unit 105 being used when natural emission light is transmitted to the optical probe 200.

(3) Reflectance of the half mirror 112 of the monitoring unit 106 has a wavelength property, that is, a larger bandwidth than the bandwidth of laser light. Because of this, more natural emission light is reflected by the half mirror 112 than laser light reflected by the half mirror 112.

(4) As a matter of course, the radiation angle of natural emission light is larger than the radiation angle of laser light. Because of this, a larger area of the photodiode 113 of the monitoring unit 106 is irradiated with natural emission light than an area irradiated with laser light. Actually, components other than the photodiode 113 are irradiated with natural emission light.

In view of these, in the PDT laser-therapy apparatus 100, calculation in a low-power range (natural-emitted-light emitting range) by the calculation unit 107 is different from calculation in a power range larger than that (laser-light emitting range) by the calculation unit 107. Because of this, calibration accuracy is improved in a wider power range.

Here, Iop is indicative of current supplied to the semiconductor laser 111. Further, a threshold current Ith is indicative of current supplied to the semiconductor laser 111 at the border between the natural-emitted-light emitting range and the laser-light emitting range, which are emitted from the semiconductor laser 111.

In the case of the natural-emitted-light emitting range (Iop<Ith), the calculation unit 107 uses the following quadratic function:

$$y=ax^2+bx+c \quad \text{(Expression 1)}$$

to thereby obtain an approximate expression showing correlation between the output from the calibration unit 102 and the output from the monitoring unit 106.

Here, y is indicative of an output (present value: P) from the calibration unit 102. x is indicative of an output (monitored value: Vmoni) from the monitoring unit 106.

In the case of the laser-light emitting range (Iop≥Ith), the calculation unit 107 uses the following linear function:

$$y=dx+e \quad \text{(Expression 2)}$$

to thereby obtain an approximate expression showing correlation between the output from the calibration unit 102 and the output from the monitoring unit 106.

Note that the above-mentioned approximate expression is obtained by using, for example, the least squares method or the like.

In the laser-light emitting range of the semiconductor laser 111, the calculation unit 107 uses a linear-function calculation expression (Expression 2) to thereby calculate a correlation between an output from the calibration unit 102 and an output from the monitoring unit 106. In the natural-emitted-light emitting range of the semiconductor laser 111, the calculation unit 107 uses a quadratic-function (non-linear) calculation expression (Expression 1) to thereby calculate a correlation between an output from the calibration unit 102 and an output from the monitoring unit 106.

Figure 7:
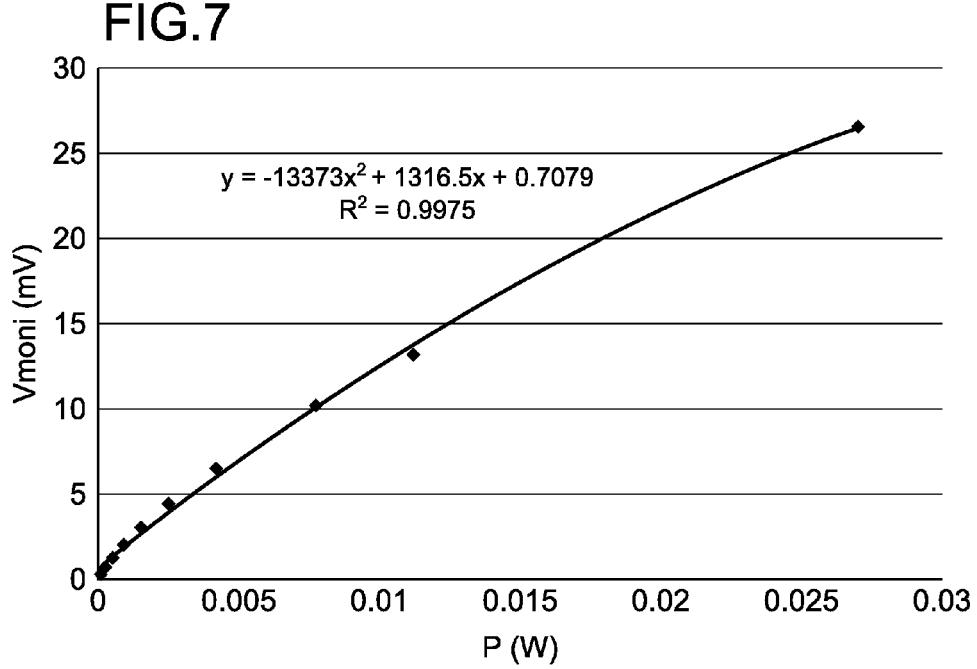
FIG. 7 is a graph showing an example in which a relation between an output from the calibration unit and an output from the monitoring unit is approximated by using a quadratic (non-linear) function in an emitting range of natural emission light from the semiconductor laser.
Figure 8:
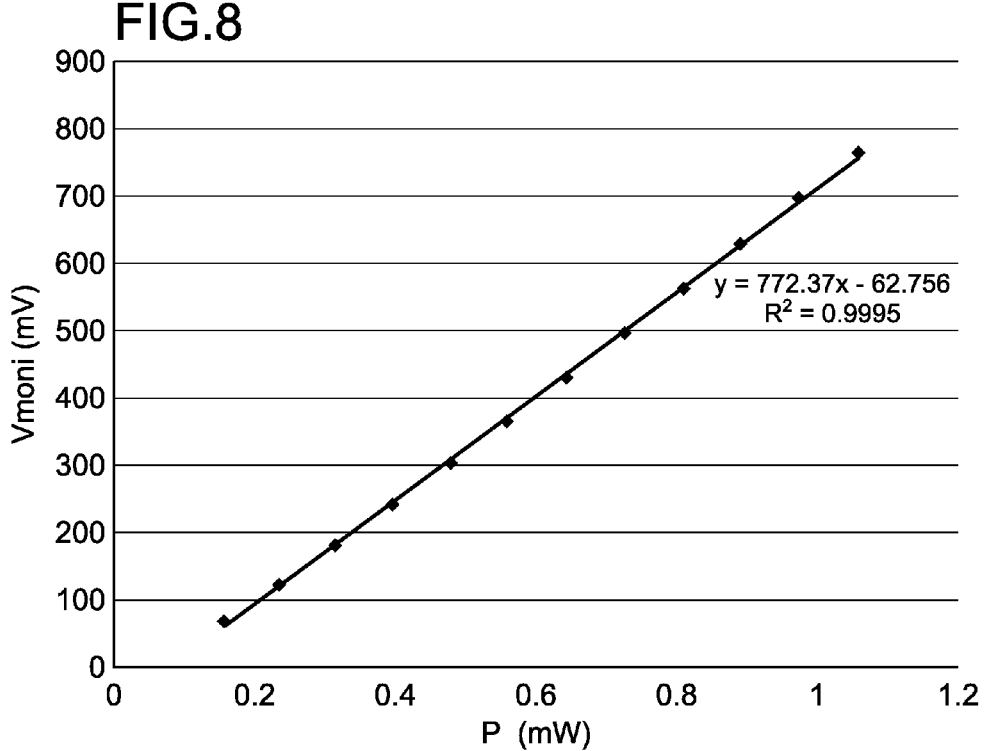
FIG. 8 is a graph showing an example in which a relation between an output from the calibration unit and an output from the monitoring unit is approximated by using a linear function in an emitting range of laser light from the semiconductor laser.

FIG. 7 shows an example in which the calculation unit 107 approximates a relation between an output (P) from the calibration unit 102 and an output (Vmoni) from the monitoring unit 106 by using a quadratic (non-linear) function in the natural-emitted-light emitting range of the semiconductor laser 111. FIG. 8 shows an example in which the calculation unit 107 approximates a relation between an output (P) from the calibration unit 102 and an output (Vmoni) from the monitoring unit 106 by using a linear function in the laser-light emitting range of the semiconductor laser 111.

In each of FIG. 7 and FIG. 8, dots shown in the vicinity of the line, which shows the function, are indicative of points actually measured during calibration.

Figure 9:
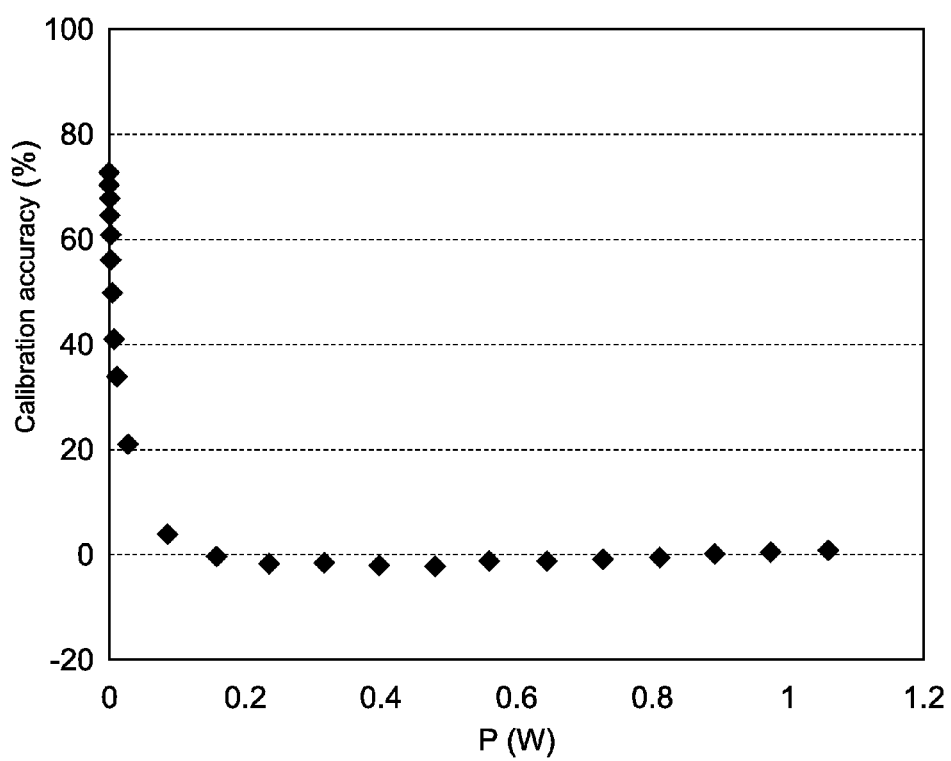
FIG. 9 is a graph showing an example of calibration accuracy in a case where calibration is performed by using a quadratic function in a low-power range, which is an emitting range of natural emission light, and by using a linear function in a high-power range, which is an emitting range of laser light.

As described above, calibration is performed by using a quadratic function in a low-power range, which is the natural-emitted-light emitting range, and calibration is performed by using a linear function in a high-power range, which is the laser-light emitting range. FIG. 9 shows an example of calibration accuracy.

In general, calibration accuracy of 20% is required for apparatus performance. As shown in FIG. 9, the range satisfying calibration accuracy of 20% is the range between 500 μW and 1 W. Meanwhile, in FIG. 3, the range satisfying calibration accuracy of 20% is the range between 65 mW and 1 W. As shown in FIG. 9, the calibration accuracy is about double-digit increased in the low-power range.

Therefore, the PDT laser-therapy apparatus 100 is capable of accurately obtaining an output of light exiting from the optical probe 200 not only during therapy but also when monitoring, for example, pharmaceutical concentration. Further, in a different viewpoint, calculation may be performed by using the small number of samples during calibration. So the calibration may be accurately performed in a short time.

Example of Optical Probe

Figure 10:
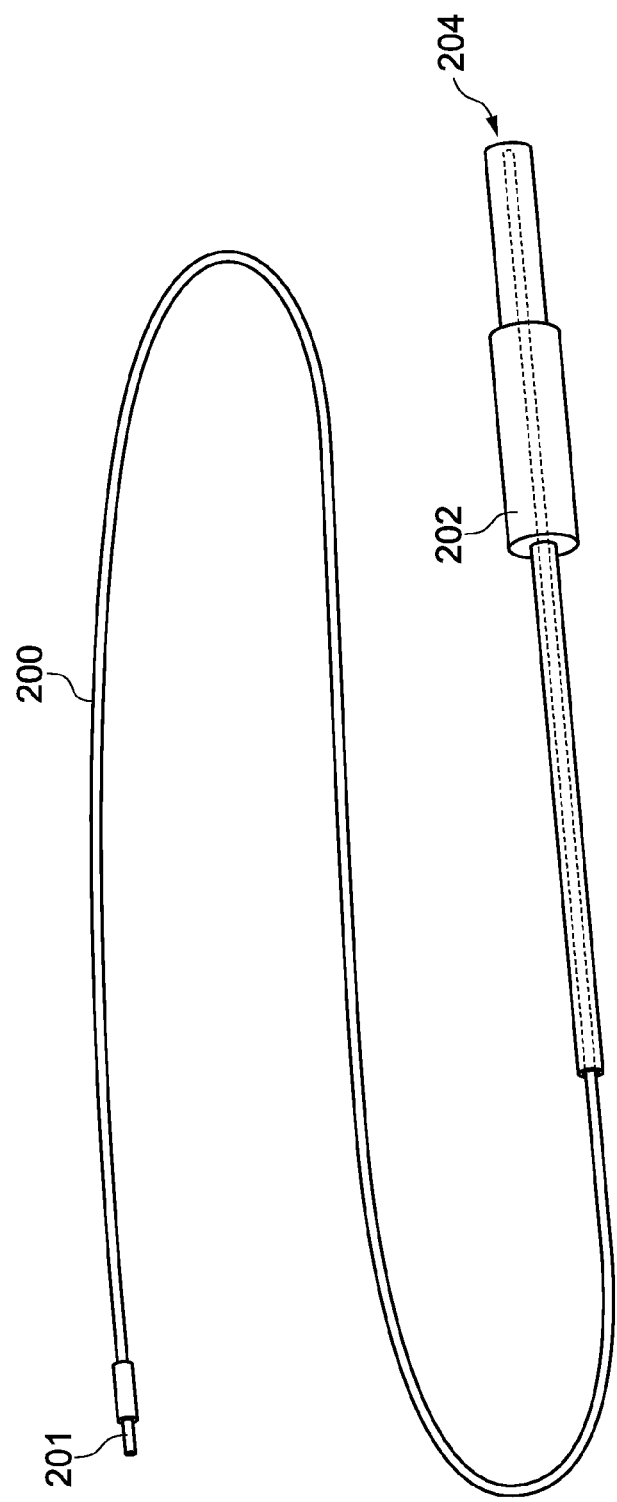
FIG. 10 is a perspective view showing an example of the optical probe.
Figure 11:
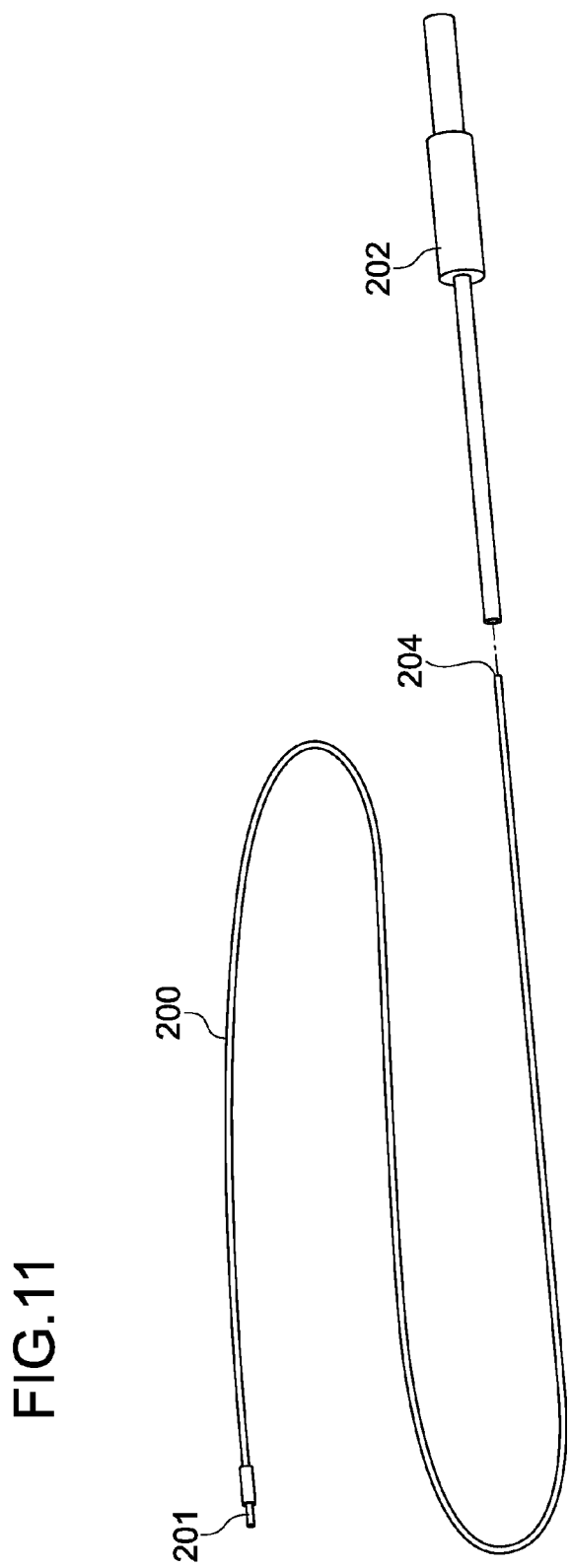
FIG. 11 is a perspective view showing a state where an applicator is removed from the optical probe of FIG. 10.

Each of FIG. 10 and FIG. 11 is a perspective view showing an example of the optical probe.

As shown in FIG. 10, the applicator 202 covers part of the optical probe 200.

The optical probe 200 is inserted in a body cavity, for example, in a blood vessel or the like. A light output unit at the tip outputs laser light and the like. Before the optical probe 200 is inserted in a body cavity, the calibration unit 102 measures an output of light exiting from the light output unit of the optical probe 200.

In this example, an output of light is measured in the state where the applicator 202 is attached to the optical probe 200. After the measurement, as shown in FIG. 11, the applicator 202 is pulled out from the optical probe 200. In this state, a procedure is performed by using the optical probe 200. The applicator 202 covers part of the optical probe 200. The covered part of the optical probe 200 is inserted in a body cavity. Because of this, the optical probe 200 does not come close to or does not contact a dirty portion of a light power meter, the optical probe 200 is not contaminated, and the optical probe 200 is kept clean.

The total length of the optical probe 200 is, for example, 3 m. The total length of the applicator 202 is, for example, about 1.1 m to 1.2 m. During a procedure, the optical probe 200 is inserted in a body by about 1 m, for example.

The optical probe 200 guides laser light and natural emission light. The optical probe 200 has, at one end, the light guiding unit 201 to be connected to the guide unit 101. The optical probe 200 has, at the other end, a light output unit 204 outputting laser light. An FC, SMA, or another-type optical connector (not shown) is provided in the light guiding unit 201. The light guiding unit 201 having such a connector is connected to the guide unit 101. The light output unit 204 is inserted in a body cavity during a procedure.

The applicator 202 covers the optical probe 200 so as to be capable of outputting laser light from the light output unit 204 of the optical probe 200 to the outside through an openable window, for example. The applicator 202 is detachable from the optical probe 200.

Figure 12:
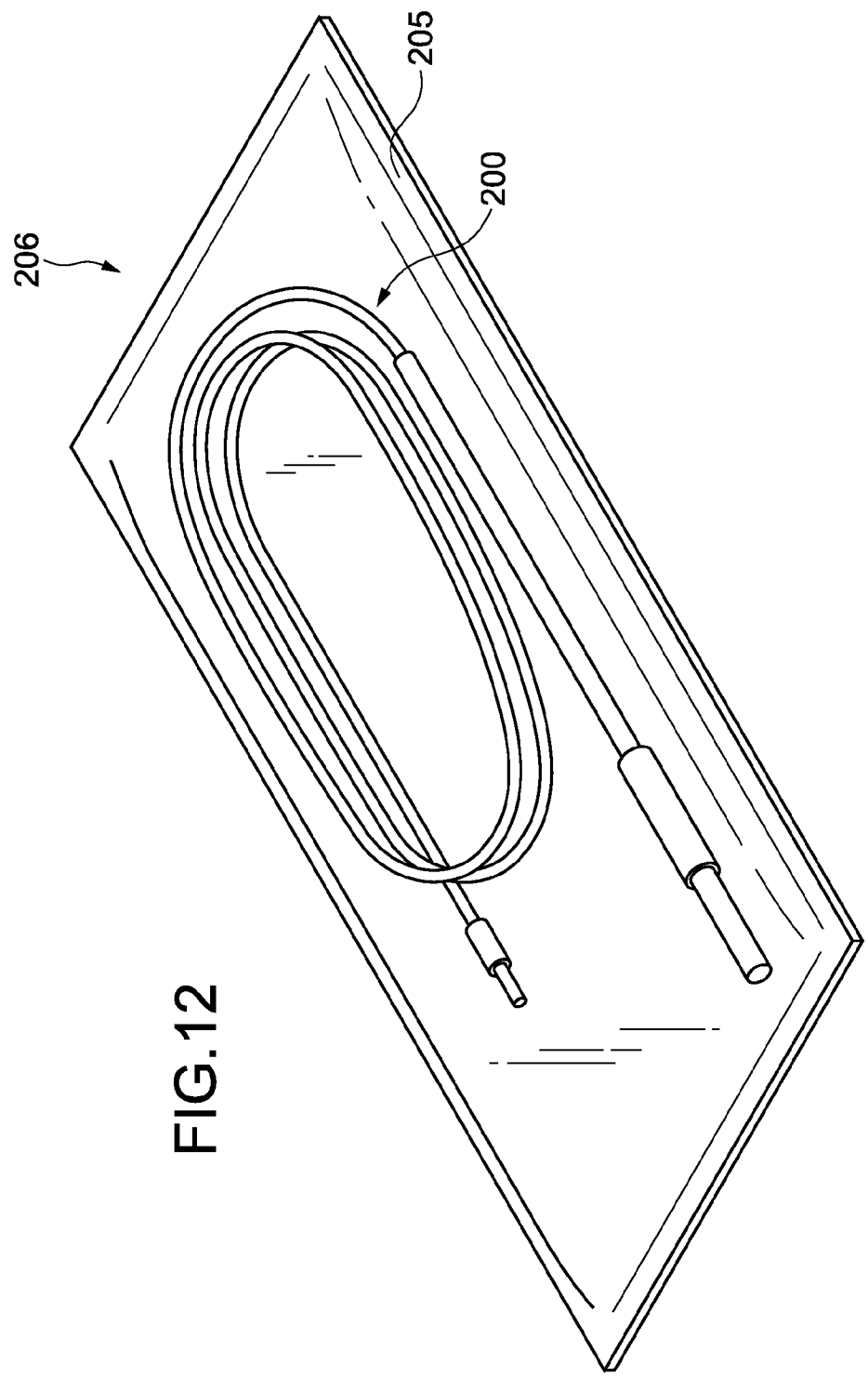
FIG. 12 is a perspective view showing a state where the optical probe of FIG. 10

Note that, as shown in FIG. 12, the optical probe 200 and a packaging material 205 are sterilized by EOG (ethylene oxide gas) or radiation, whereby an optical probe package 206 is prepared. The optical probe 200 is supplied to a medical institution in the state of the optical probe package 206. When used, the packaging material 205 is opened, and the optical probe 200 is taken out.

Calibration Process

Next, a calibration process for the PDT laser-therapy apparatus 100 configured as described above will be described.

Figure 13:
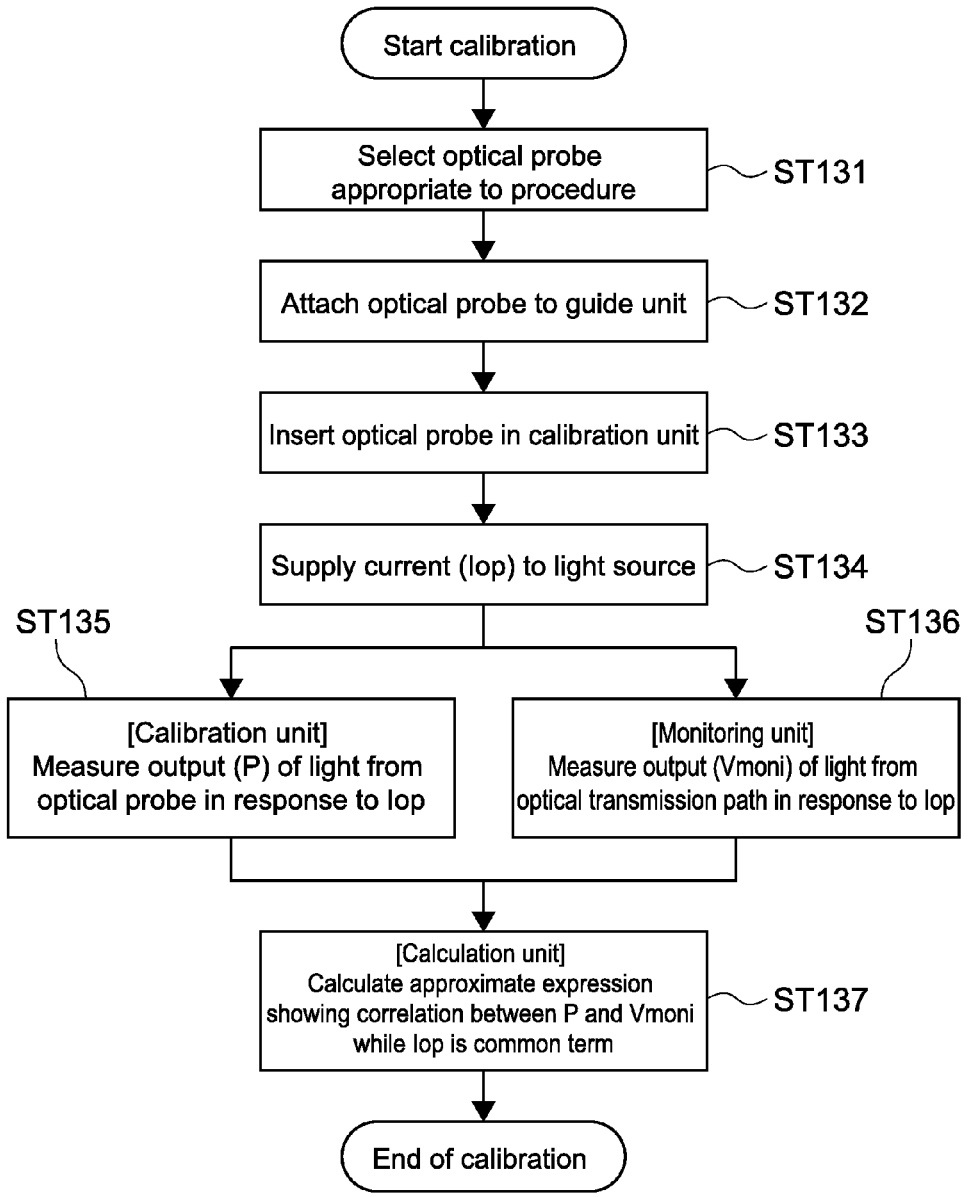
FIG. 13 is a flowchart showing calibration process according to the embodiment of the present application in detail.

FIG. 13 is a flowchart showing a calibration process in detail.

A plurality of kinds of optical probes 200, which have different diameters, for example, are prepared. An operator selects the optical probe 200 appropriate to a procedure (Step 131).

Figure 14:
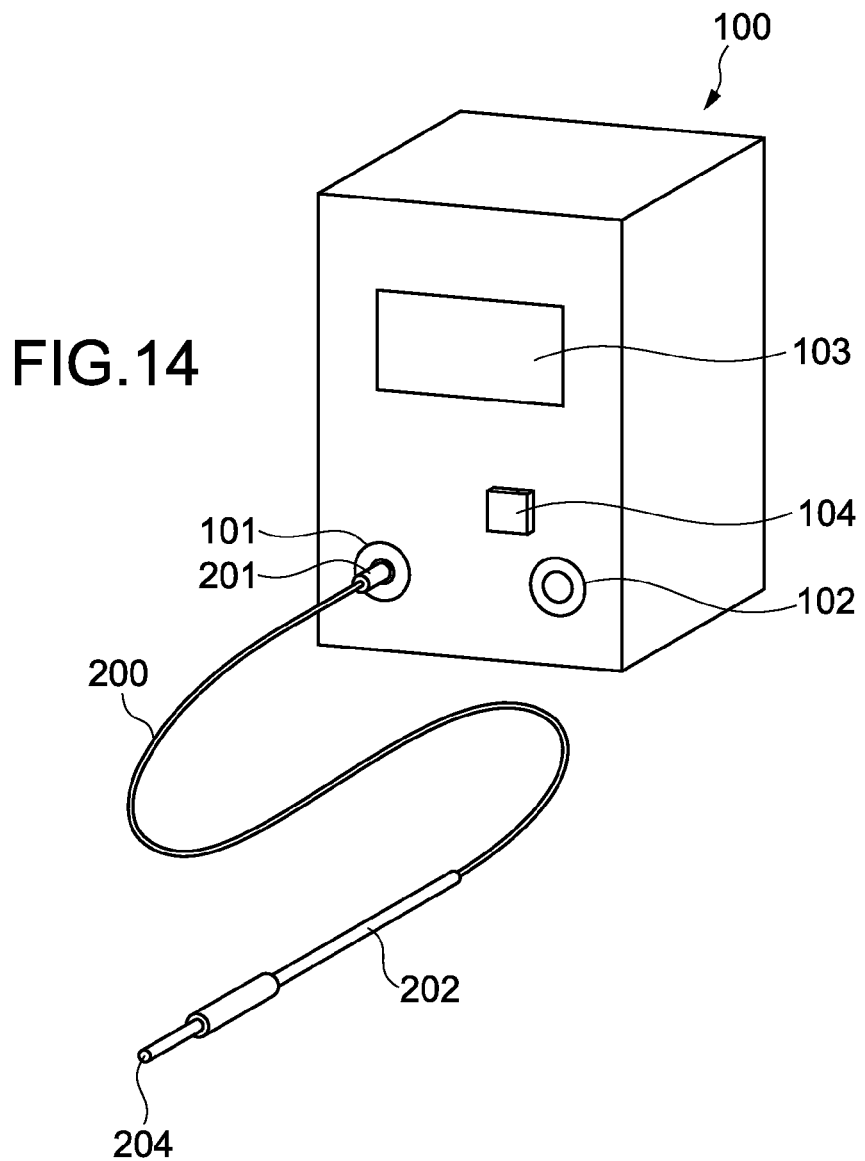
FIG. 14 is a perspective view showing an outer appearance of a PDT laser-therapy apparatus in a state where a light guiding unit, which is at one end of the optical probe, is attached to a guide unit.

Next, as shown in FIG. 14, an operator attaches the light guiding unit 201, which is at the one end of the optical probe 200, to the guide unit 101 in the state where the applicator 202 is attached to secure a clean area (Step 132).

Next, as shown in FIG. 1, an operator inserts the light output unit 204, which is the other end of the optical probe 200, in the calibration unit 102 in the state where the applicator 202 is attached (Step 133).

Next, current (Iop) is supplied to the semiconductor laser 111 of the light source unit 105 (Step 134). After that, the current (Iop) value is caused to be increased gradually. Alternatively, the current (Iop) value is caused to be decreased gradually. Alternatively, another setting method may be used.

The calibration unit 102 measures an output (P) of light from the optical probe 200 in response to the current (Iop) supplied to the semiconductor laser 111 (Step 135). FIG. 4 shows an example of the result.

Similarly, the monitoring unit 106 also measures an intensity (Vmoni) of light to the optical probe 200 in response to the current (Iop) supplied to the semiconductor laser 111 (Step 136). FIG. 5 shows an example of the result.

The calculation unit 107 calculates an approximate expression showing a correlation between the measured output (P) of light from the optical probe 200 and the measured intensity (Vmoni) of light to the optical probe 200 while a current (Iop) supplied to the semiconductor laser 111 is a common term (Step 137).

When the calculation unit 107 calculates the approximate expression, if the current (Iop) supplied to the semiconductor laser 111 is equal to or smaller than the threshold current Ith, the calculation unit 107 uses a quadratic function, which is a non-linear function, to calculate the approximate expression. If the current (Iop) supplied to the semiconductor laser 111 is larger than the threshold current Ith, the calculation unit 107 uses a linear function to calculate the approximate expression.

In the example of FIG. 7, the following approximate expression is calculated.

$$y=-13373x^2+1316.5x+0.7079$$

In the example of FIG. 8, the following approximate expression is calculated.

$$y=772.37x-62.756$$

This is the end of the calibration process.

The calculation unit 107 stores the two approximate expressions calculated as described above as expressions to calibrate the optical probe 200 being connected.

Procedure in Which PDT Laser-Therapy Apparatus is Used

After the calibration process is finished, a procedure is performed.

Figure 15:
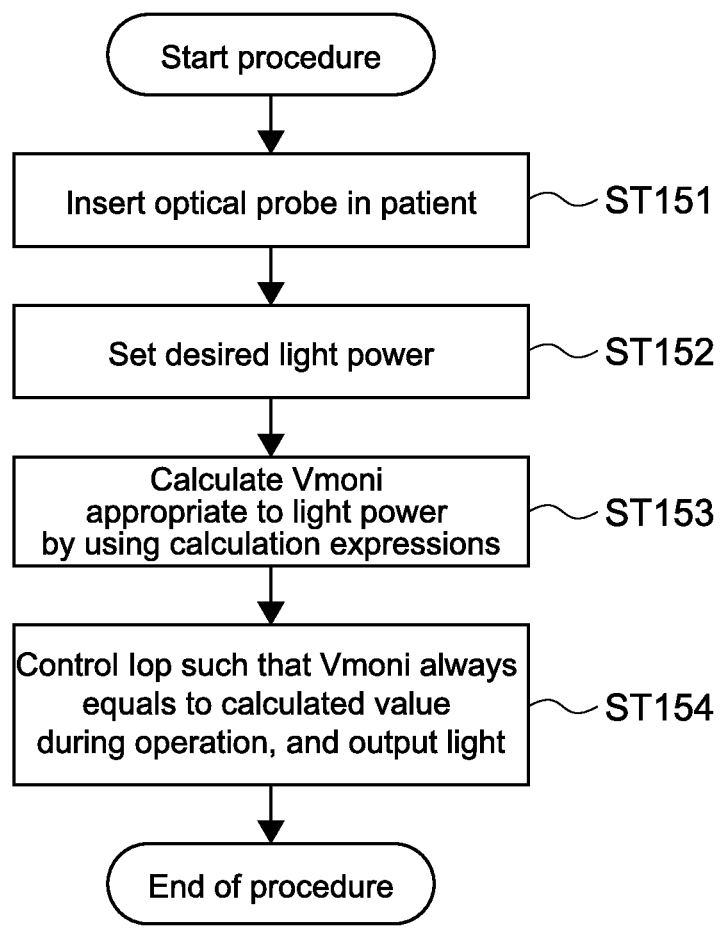
FIG. 15 is a flowchart showing a procedure using the PDT laser-therapy apparatus according to the embodiment of the present application.

FIG. 15 is a flowchart of a procedure using the PDT laser-therapy apparatus 100 configured as described above.

Figure 16:
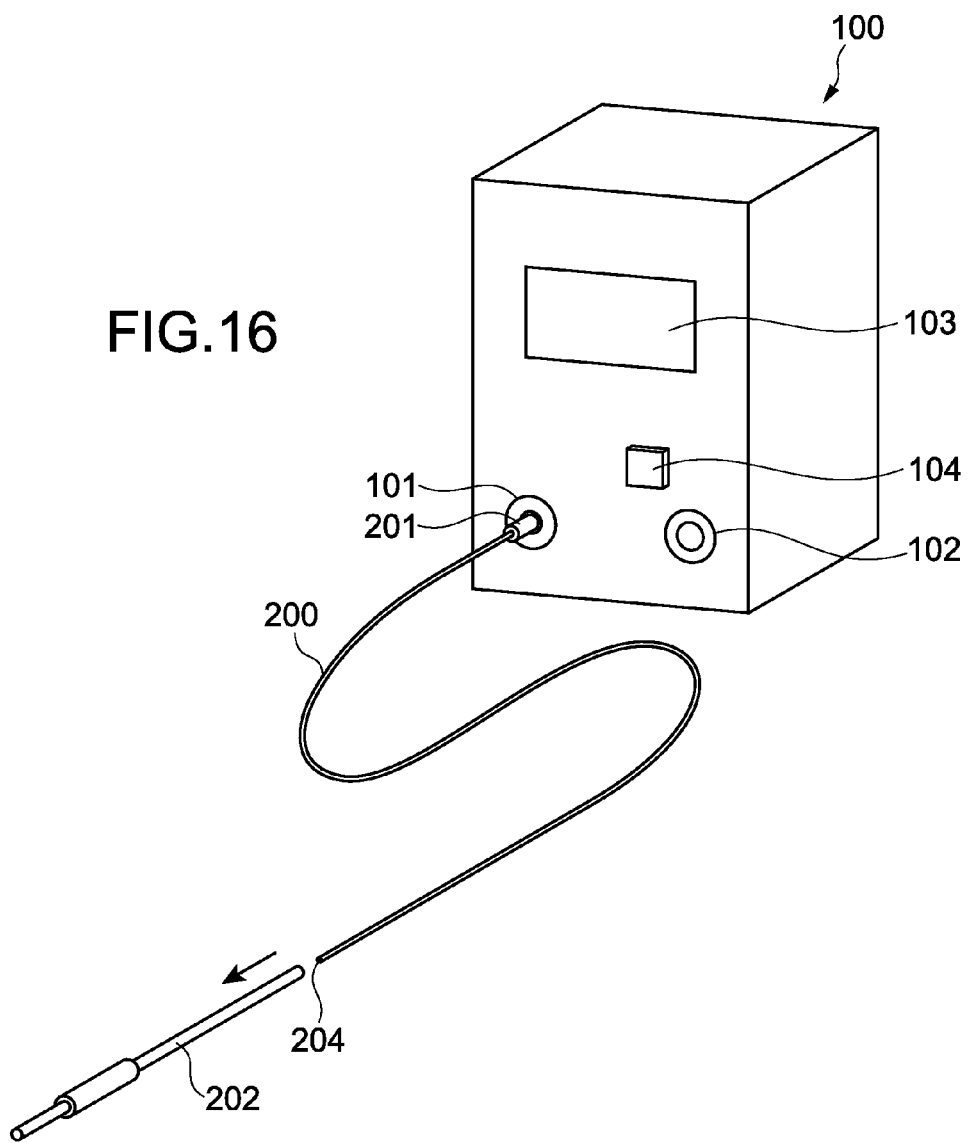
FIG. 16 is a perspective view showing an outer appearance of the PDT laser-therapy apparatus in a state where an applicator 202 is removed from the optical probe.

As shown in FIG. 16, an operator removes the applicator 202 from the optical probe 200, and inserts the optical probe 200 in a patient (Step 151).

Next, an operator operates the operation unit 108 to thereby set an output of light exiting from the optical probe 200 (Step 152).

Here, a monitored value (Vmoni), which is appropriate to the output (P) of light, is calculated by using the calculation expressions, which are calculated by the calculation unit 107 during calibration (Step 153).

The calculation unit 107 controls the current (Iop) supplied to the semiconductor laser 111 such that the monitored value (Vmoni) equals to a calculated value during operation. The calculation unit 107 causes the semiconductor laser 111 to output light (Step 154).

Therefore, the PDT laser-therapy apparatus 100 is capable of stably obtaining a desired output of light from the optical probe 200, not only during therapy but also when monitoring pharmaceutical concentration, for example.

Another Embodiment

Figure 17:
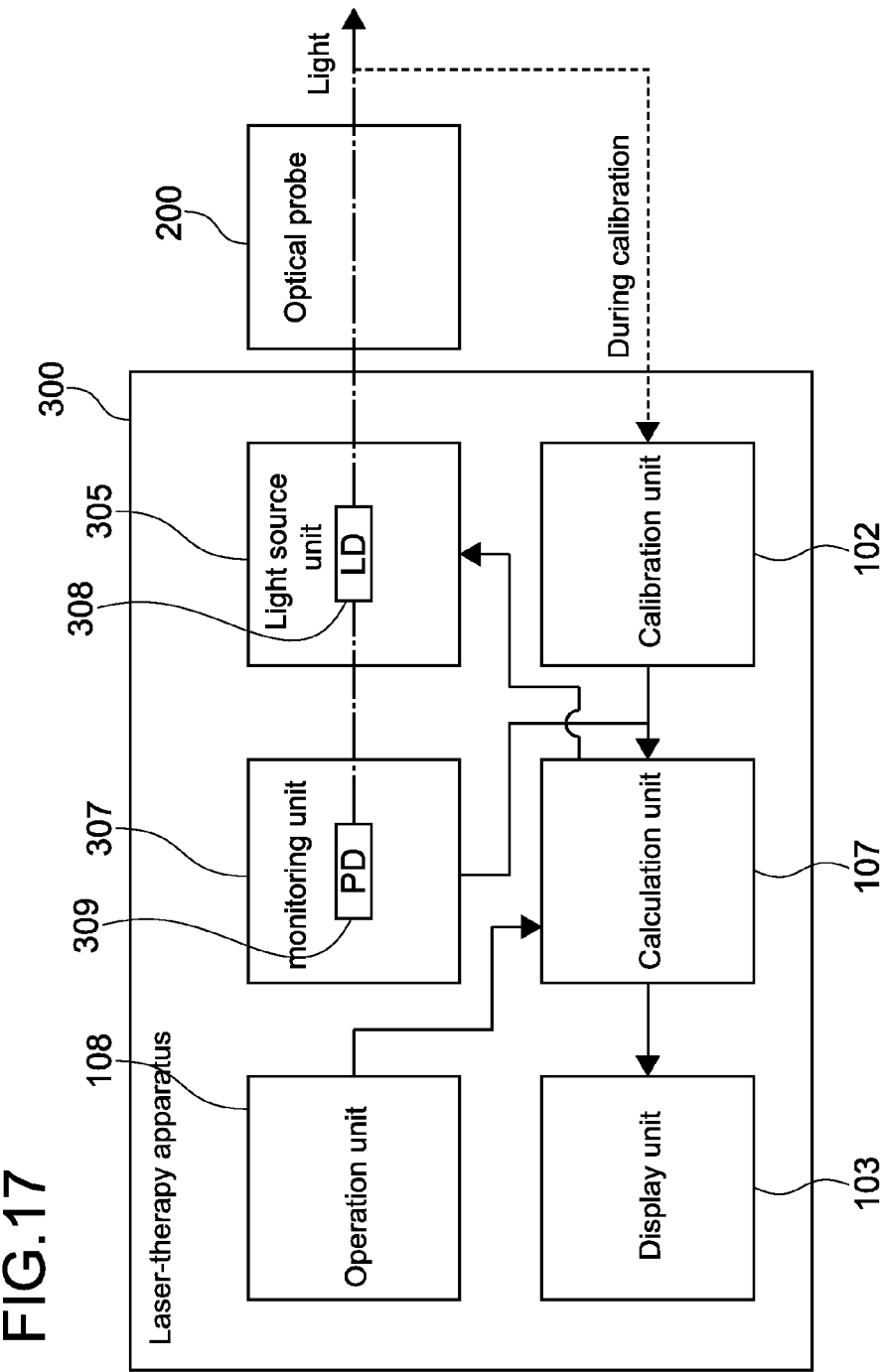
FIG. 17 is a block diagram showing the configuration of a PDT laser-therapy apparatus according to another embodiment of the present application.

FIG. 17 is a block diagram showing the configuration of a PDT laser-therapy apparatus according to another embodiment. Note that, in the embodiment shown in FIG. 17, structural elements same as the structural elements of the above-mentioned embodiment will be denoted by the same reference numerals.

As shown in FIG. 17, a PDT laser-therapy apparatus 300 has a monitoring unit 307. The monitoring unit 307 has a structure different from that of the above-mentioned embodiment. The monitoring unit 307 has a monitoring photodiode 309. The monitoring photodiode 309 detects an intensity of light partially output from the side opposite to the light-output side of a semiconductor laser 308, which is provided in a light source unit 305.

An intensity of light detected by the monitoring photodiode 309 is sent to the calculation unit 107 as a monitored value (Vmoni). Similar to the above-mentioned embodiment, the calculation unit 107 uses the monitored value (Vmoni) for calibration and therapy.

According to the PDT laser-therapy apparatus 300 configured as described above, the monitoring unit 307 includes no half mirror. So the number of components is reduced. Further, an optical property of natural emission light, which an optical component such as a half mirror guides to a monitoring photodiode, may be different from an optical property of laser light, which an optical component such as a half mirror guides to a monitoring photodiode. Such a fact degrades calibration accuracy. However, the PDT laser-therapy apparatus 300 does not include such an optical component. As a result, calibration accuracy is improved.

Others

The present application is not limited to the above-mentioned embodiments, and may be implemented in various modes, to which modifications are applied. The scope of the present application includes such various modifications.

For example, in the above-mentioned embodiments, the present application is applied to a PDT laser-therapy apparatus for atrial fibrillation. Alternatively, the present application may be applied to a laser-therapy apparatus for a heart and the like.

Further, in the above-mentioned embodiments, a semiconductor laser is employed and is described as an optical device for emitting light, which is in the light source unit. Alternatively, an optical device other than a semiconductor laser may be used, as a matter of course. For example, a light emitting diode (LED) may be used instead of a semiconductor laser. A medical apparatus according to the present application, which includes a light emitting diode in the light source unit, may be used as an inspection apparatus for monitoring pharmaceutical concentration, not as a therapy apparatus, for example.

The present application may employ the following configurations.

(1) A medical apparatus, comprising:
a light source unit configured to be capable of emitting light including at least natural emission light, the light being guided into an optical probe;
a first detecting unit configured to detect an intensity of light exiting from the light source unit; and
a calculation unit configured to calculate to approximate to a non-linear function based on an intensity of light detected by the first detecting unit for calibration of the optical probe.

(2) The medical apparatus according to (1), wherein
the light source unit includes a semiconductor laser, and
the calculation unit is configured to, in a case where the semiconductor laser emits light including laser light, calculate to approximate to a linear function based on an intensity of light detected by the first detecting unit for calibration of the optical probe.

(3) The medical apparatus according to (1) or (2), wherein
the calculation unit is configured to determine whether the semiconductor laser emits light including the natural emission light or the semiconductor laser emits light including the laser light, based on a laser-oscillation-threshold current from the semiconductor laser.

(4) The medical apparatus according to any one of (1) to (3), further comprising:
a guide unit, to which the optical probe is attachable, configured to guide light emitted from the light source unit to the attached optical probe; and
a second detecting unit configured to detect an output of light exiting from the optical probe attached to the guide unit, wherein
the calculation unit is configured to obtain a correlation between an intensity of light detected by the first detecting unit and an output of light detected by the second detecting unit, based on calculation to approximate to the non-linear function.

(5) The medical apparatus according to (4), wherein
the calculation unit is configured to calculate an output of light exiting from the optical probe based on an intensity of light detected by the first detecting unit by using the obtained correlation.

(6) The medical apparatus according to (5), further comprising:
a display unit configured to display an output of light exiting from the optical probe, the output of light being calculated by the calculation unit; and
an operation unit configured to be capable of receiving an operation to adjust an output of light emitted from the light source unit.

(7) A therapy apparatus, comprising:
a semiconductor laser;
a guide unit, to which one end of an optical probe is attachable, configured to guide light from the semiconductor laser to the one end;
a calibration unit, to which the other end of the optical probe is inserted when calibrating the optical probe, configured to detect an output of light from the other end; and
a calculation unit configured to obtain a correlation between an intensity of light from the semiconductor laser and an output of light detected by the calibration unit, based on calculation to approximate to a linear function when the semiconductor laser emits laser light, and based on calculation to approximate to a non-linear function when the semiconductor laser emits natural emission light.

(8) A method of estimating an optical probe, comprising:
introducing light into one end of an optical probe;
guiding light out of the other end of the optical probe; and
obtaining a correlation between an intensity of the introduced light and an output of the guided light for each optical probe, based on calculation to approximate to a non-linear function.

(9) The method of estimating an optical probe according to (8), further comprising:
obtaining a correlation between an intensity of the introduced light and an output of the guided light based on calculation to approximate to a linear function, in a case where light introduced into the optical probe is laser light.

(10) A calibration method, comprising:
guiding light from a semiconductor laser into one end of an optical probe;
detecting an output of light from the other end of the optical probe; and
obtaining a correlation between an intensity of light from the semiconductor laser and the detected output of light, based on calculation to approximate to a linear function when the semiconductor laser emits laser light, and based on calculation to approximate to a non-linear function when the semiconductor laser emits natural emission light.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A medical apparatus, comprising:
   a light source unit configured to emit a light selected from the group consisting of a first light and a second light, the light source unit configured to emit the first light when a first current is supplied to the light source unit and emit the second light when a second current is supplied to the light source unit, wherein the first current is equal to or smaller than a laser-oscillation-threshold current, and the second current is larger than the laser-oscillation-threshold current;
   a first detecting unit connected to the light source unit;
   an optical probe connected to the first detecting unit, wherein the first detecting unit is configured to detect a light intensity from a part of the light exiting from the light source unit and entering the optical probe; and
   a calculation unit configured to calculate an output of the light exiting from the optical probe, based on the light intensity detected by the first detecting unit, using a first function when the light source unit emits the first light and using a second function different from the first function when the light source unit emits the second light.

2. The medical apparatus according to claim 1, wherein the light source unit includes a semiconductor laser.

3. The medical apparatus according to claim 1, further comprising a guide unit, to which the optical probe is attachable, that guides light emitted from the light source unit to the attached optical probe.

4. The medical apparatus according to claim 3, wherein the calculation unit is configured to obtain a correlation between the light intensity and the output of light, based on calculation to the first function when the light source unit emits the first light and based on calculation to the second function when the light source unit emits the second light.

5. The medical apparatus according to claim 4, further comprising:
   a display unit that displays an output of light exiting from the optical probe, the output of light being calculated by the calculation unit; and
   an operation unit capable of receiving an operation to adjust an output of light emitted from the light source unit.

6. A therapy apparatus, comprising:
   a light source unit configured to emit a light selected from the group consisting of a first light and a second light, the light source unit configured to emit the first light when a first current is supplied to the light source unit and emit the second light when a second current is supplied to the light source unit, wherein the first current is equal to or smaller than a laser-oscillation-threshold current, and the second current is larger than the laser-oscillation-threshold current;
   an optical probe;
   a guide unit, to which one end of the optical probe is attachable, wherein the guide unit guides the light from the light source unit to the one end of the optical probe;
   a calibration unit that detects an output of the light from the other end of the optical probe; and
   a calculation unit configured to calculate the output of the light exiting from the optical probe using a first function when the light source unit emits the first light and using a second function different from the first function when the light source unit emits the second light.

7. The medical apparatus according to claim 1, wherein the first detecting unit comprises a half mirror and a photodiode.

8. The medical apparatus according to claim 1, further comprising a calibration unit configured to detect the output of light exiting from the optical probe.

9. The medical apparatus according to claim 3, further comprising a second detecting unit that detects a second output of light exiting from the optical probe attached to the guide unit, wherein the calculation unit is configured to obtain a correlation between the light intensity detected by the first detecting unit and the second output of light detected by the second detecting unit.

10. The medical apparatus according to claim 1, wherein the first function is a non-linear function, and the second function is a linear function.

* * * * *